United States Patent [19]

Longo et al.

[11] Patent Number: 4,876,045
[45] Date of Patent: Oct. 24, 1989

[54] PROCESS FOR THE PREPARATION OF METHYLENE DERIVATIVES OF ANDROSTA-1,4-DIENE-3,17-DIONE

[75] Inventors: Antonio Longo; Paolo Lombardi, both of Milan, Italy

[73] Assignee: Farmitalia Carlo Erba S.r.l., Milan, Italy

[21] Appl. No.: 242,854

[22] Filed: Sep. 12, 1988

[30] Foreign Application Priority Data

Sep. 11, 1987 [GB] United Kingdom ............... 8721383

[51] Int. Cl.$^4$ .................................................. C07J 1/00
[52] U.S. Cl. .................................................. 260/397.3
[58] Field of Search ..................... 514/177; 260/397.3

[56] References Cited

U.S. PATENT DOCUMENTS 4,808,616 2/1989 Buzzetti et al. .................. 260/397.3

OTHER PUBLICATIONS

Chemical Abstracts; vol. 109 (1988) #67168y; Giudici et al.
Chemical Abstracts; vol. 108 (1988) #2211966v; Buzzetti et al.
Chemical Abstracts; vol. 106 (1987) #162586e, Di Salle et al.
Tetrahedron, vol. 20 pp. 597–609 (1964).
Synthesis, pp. 34–40 (1982).

*Primary Examiner*—Douglas W. Robinson
*Assistant Examiner*—Joseph A. Lipovsky
*Attorney, Agent, or Firm*—Armstrong, Nikaido, Marmelstein, Kubovcik & Murray

[57] ABSTRACT

The invention relates to a new process for the preparation of known aromatase inhibitors of the following formula

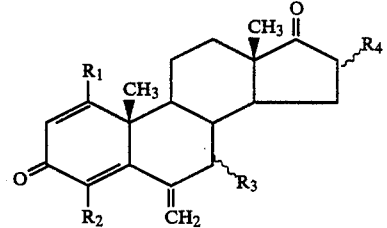

wherein
each of $R_1$ and $R_3$, independently, is hydrogen or $C_1$–$C_6$ alkyl;
$R_2$ is hydrogen, halogen or $C_1$–$C_6$ alkyl and
$R_4$ is hydrogen or fluorine; the process comprising subjecting to Mannich reaction a compound of formula

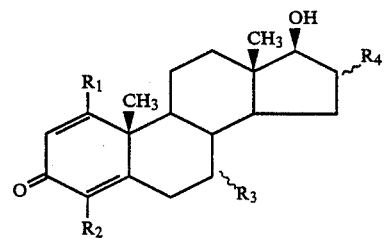

wherein
$R_1, R_2, R_3$ and $R_4$ are as defined above, and then oxidizing the respective 6-methylene derivative thus obtained by methods known per se.

4 Claims, No Drawings

PROCESS FOR THE PREPARATION OF METHYLENE DERIVATIVES OF ANDROSTA-1,4-DIENE-3,17-DIONE

The introduction of a methylene, i.e. $CH_2=$, group at the 6-position of 3-oxo-$\Delta^4$-steroids is a well known process in the art. This type of substitution has been previously achieved by procedures involving a many steps synthesis. The method described by D. Burn et al. in Tetrahedron 20, 597 (1964), for instance, requires the initial conversion of a 3-oxo-$\Delta^4$-steroid into its 3,5-dienol ether, which is then subjected to Vilsmeier conditions (phosphoryl chloride/dimethylformamide) to yield the iminium salt. After hydrolysis, reduction, and dehydration, the 6-methylene derivative is obtained: Scheme A.

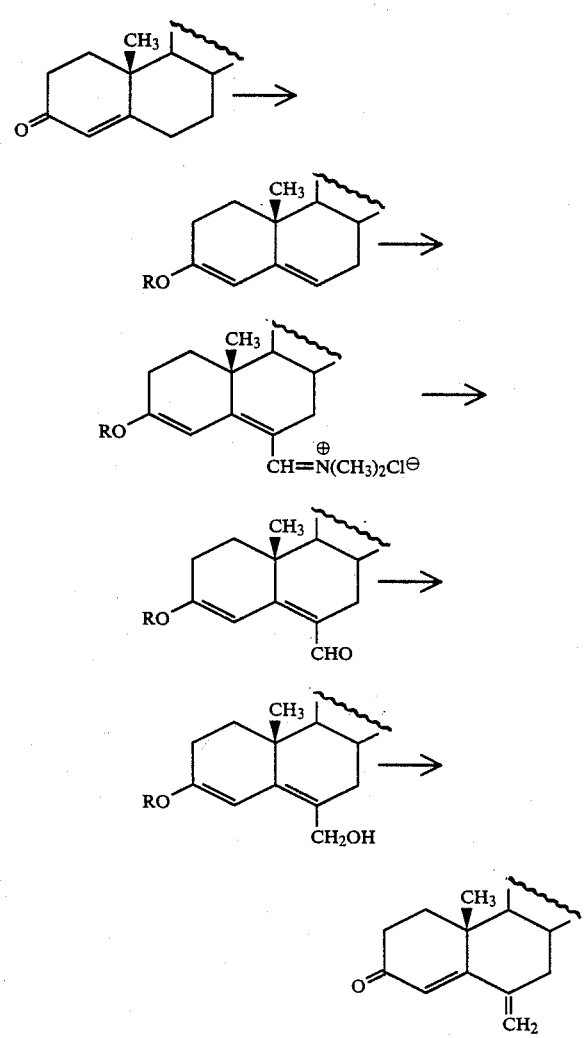

wherein R is lower alkyl.

Published British patent application No. 2177700 and European patent application No. 87306125.3 disclose 6-methylene derivatives of androsta-1,4-diene-3,17-dione, which are inhibitors of the biotransformation of endogenous androgens to estrogens, i.e. they are aromatase inhibitors. These compounds are useful, e.g., in the treatment of hormone-dependent tumors, such as breast, endometrial and ovarian cancers.

In the above-mentioned patent applications the methylenation step synthesis is carried out according to the method of K. Annen et al. described in Synthesis 1982, 34: Scheme B.

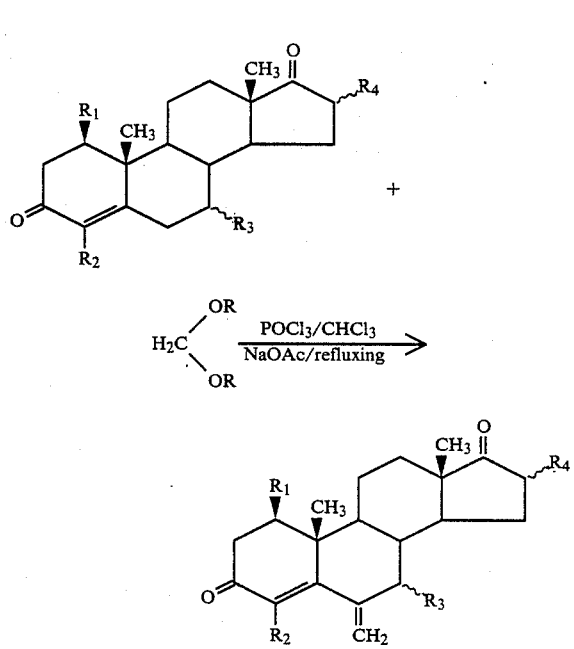

wherein
each of $R_1$ and $R_3$, independently, is hydrogen or $C_1$-$C_6$ alkyl;
$R_2$ ;l is hydrogen, halogen or $C_1$-$C_6$ alkyl;
$R_4$ is hydrogen or fluorine; and R is a lower alkyl group.

The use of formaldehyde acetals with longer or branched alkoxy groups results in a lower yield of product. Although this method for direct methylenation of 3-oxo-$\Delta^4$ steroids provides an economical method for the introduction of a 6-methylene group, it is not possible to obtain yields of products higher than about 40–45%. Furthermore, if the whole process for the preparation of the corresponding 6-methylenandrosta-1,4-diene-3,17-diones, described in the above-mentioned patent applications, is considered, it has to be noticed that:

a. The obtained 3-oxo-6-methylene-$\Delta^4$-steroids required to be submitted to a long-lasting column chromatography purification, before being dehydrogenated to the corresponding 6-methylene-$\Delta^{1,4}$-derivatives.

b. The best oxidizing agent used in the dehydrogenation step synthesis is dichlorodicyanobenzoquinone (DDQ), that is very expensive.

c. The dehydrogenation step synthesis provides yields of end-products not higher than about 40–50%.

d. The obtained end-products require a further long-lasting column chromatography purification. Hence the process described in the above-mentioned patent applications provides yields of about 20–25% of end-products. It requires two long-lasting column chromatography separations; and what is the more the best reducing agent, i.e. DDQ, is very expensive. It appears clear that this process cannot be advantageously used for large-scale production. In investigating both different methods and different intermediate products for preparing compounds described in the above-mentioned applications and having the following formula (I)

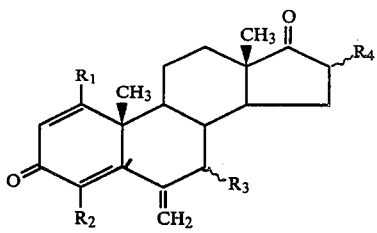

wherein $R_1$, $R_2$, $R_3$ and $R_4$ are as defined above, we noticed the method for direct γ-methylenation of 3-oxo-Δ⁴-steroids is applicable to a very wide variety of substrates but not to androsta-1,4-diene-3,17-dione derivatives.

A very interesting observation has been made in the case of androsta-1,4-dien-17β-ol-3-one derivatives. Indeed surprisingly an androsta-1,4-dien-17β-ol-3-one derivative can be subjected to Mannich reaction and the obtained 6-methylene-product can easily be oxidized to an end-product of formula (I), as above defined.

The present invention relates therefore to a new process for the preparation of compounds of formula (I), as herein defined, the process comprising reacting a compound of formula (II)

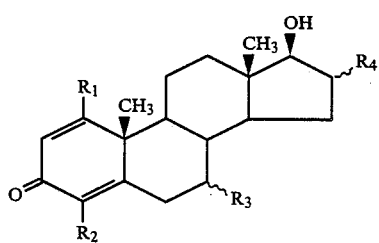

wherein $R_1$, $R_2$, $R_3$ and $R_4$ are as defined above, with a formaldehyde source, preferably paraformaldehyde, and an amine of formula (III), or a salt thereof,

wherein
each R group, which may be the same or different, is lower alkyl, so as to obtain a compound of formula (IV)

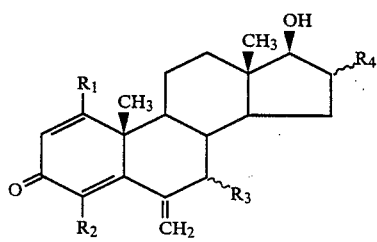

wherein $R_1$, $R_2$, $R_3$ and $R_4$ are as defined above, and then oxidizing a compound of formula (IV), thus obtained. In the formalae of the specification the heavy solid lines (—) indicate that a substituent is in the β-configuration, i.e. above the plane of the ring; a wavy line (⁓) indicates that a substituent may be either in the α-configuration, i.e. below the plane of the ring, or in the β-configuration or in both, i.e. a mixture thereof. In a compound of formula (III) R lower alkyl is e.g. $C_1$–$C_4$ alkyl, preferably it is methyl or ethyl, in particular methyl. A salt of a compound of a formula (III) is e.g. a salt with a n inorganic acid, preferably a hydrohalic acid, in particular the hydrochloric acid.

The reaction of a compound of formula (II) with the formaldehyde source and a salt of a compound of formula (III) is preferably carried out in a high boiling alcohol, in particular isopentanol, at temperatures from about 130° C. to about 150° C., and for reaction time ranging from about 3 hours to about one day. The molar ratio of the reactants (a) the compound of formula (II) (b) the formaldehyde source and (c) the amine of formula (III) is preferably 1, from about 10 to 12, and from about 12 to about 14, respectively (that is, the molar ratio of a:b:c is about 1:10–12:12–14).

In a preferred embodiment of the invention the formaldehyde source is first reacted with a salt of a compound of formula (III) and then, to the Mannish salt so obtained, a compound of formula (II) is added.

Oxidation of a compound of formula (IV) can be carried out according to well known methods, e.g. by Jones or Moffat reagents or by treatment with pyridine dichromate, in polar solvents, such as acetone, dimethyl-formamide, dimethyl-sulfoxide or acetic anhydride. The reaction temperature may range from about −30° C. to about 50° C. and the reaction may take from about 1 hour to about 1 day. Preferably oxidation of a compound of formula (IV) is carried out through Jones reagent, in acetone, at about −10° C. The specific means of accomplishing the oxidation of the compound of formula (IV) is not critical, and other conventional oxidation methods may be used if desired.

Even if the new process of this invention allows to obtain the desired products of formula (I) in similar, or slightly higher, yields (25–35%), it has the important advantage over the prior art of being both cheap and workable for large scale production. In fact the intermediate compounds of formula (II) are either commercially available products or can be obtained easily from them. For example, the compound of formula (II) wherein $R_1$, $R_2$, $R_3$ and $R_4$ are hydrogen is the commercially available product boldenone, whereas other compounds of formula (II) may be obtained from commercial available products following well known procedures in steroid chemistry as described e.g. in Fried Edwards, Organic Reactions in Steroid Chemistry, Van Nostrand Reinhold; or Djerossi, Steroid Reactions, Holden-Day, Inc. Furthermore the new process does not need any column chromatography separation.

The following Examples illustrate but do not limit the invention.

EXAMPLE 1

6-Methylenandrosta-1,4-dien-17β-ol-3-one

[compound (IV): $R_1=R_2=R_3=R_4=H$]

A stirred mixture of 106.2 g (3.54 mol) of paraformaldehyde and 346.4 g (4.248 mol) of dimethylamine hydrochloride in 3.6 l of isopentanol is refluxed (temperature of about 131° C.) under nitrogen atmosphere in a flask fitted with a Dean-Stark separator. About 900 ml of a mixture of isopentanol and separated water are collected and discarded. The internal reaction temperature is then lowered of 10°–15° C. and 90 g (0.314 mol) of boldenone (i.e. androsta-1,4-dien-17β-ol-3-one) are added to the reaction mixture, which is again heated at reflux for 15 hours.

After cooling, the mixture is treated with 1.2 l of a 0.1N NaOH solution and stirred for 30 min. The organic phase is separated, washed with water and evaporated under vacuum (external temperature of 80° C.) to yield about 1.6 l of a suspension.

The supernatant liquor is separated; the resulting precipitate is washed twice with 100 ml portions of hexane and then crystallized from 500 ml of a mixture of ethanol and water (70:30). The filtered white precipitate is dried under vacuum at 40° C., thus obtaining 28.7 g (0.963 mol; yield 30.7%) of the title product, m.p. 135°–137° C.

NMR (CDCl$_3$, δ): 0.82 (3H, s), 1.15 (3H, s), 3.67 (1H, m), 4.97 (2H, m), 6.23 (2H, m), 7.08 (1H, d) According to the above described procedure and starting from the appropriate compound of formula (II) one can prepare also the following compounds:
1-methyl-6-methylenandrosta-1,4-dien-17β-ol-3-one;
1-ethyl-6-methylenandrosta-1,4-dien-17B-ol-3-one;
4-methyl-6-methylenandrosta-1,4-dien-17β-ol-3-one;
4-chloro-6-methylenandrosta-1,4-dien-17β-ol-3-one;
4-bromo-6-methylenandrosta-1,4-dien-17β-ol-3-one;
4-fluoro-6-methylenandrosta-1,4-dien-17β-ol-3-one;
4-chloro-1-methyl-6-methylenandrosta-1,4-dien-17β-ol-3-one;
4-bromo-1-methyl-6-methylenandrosta-1,4-dien-17β-ol-3-one;
4-fluoro-1-methyl-6-methylenandrosta-1,4-dien-17β-ol-3-one;

Analogously one can obtain the following 7-and/or 16-substituted derivatives as single epimers or as a mixture thereof
1,7-dimethyl-16-fluoro-6-methylenandrosta-1,4-dien-17β-ol-3-one;
16-fluoro-6-methylenandrosta-1,4-dien-17β-ol-3-one;
16-fluoro-1-mthyl-6 methylenandrosta-1,4-dien-17β-ol-3-one;
1,7-dimethyl-6-methylenandrosta-1,4-dien-17β-ol-3-one
16-fluoro-7-methyl-6-methylenandrosta-1,4-dien-17β-ol-3-one;
4,16-difluoro-1,7-dimethyl-6-methylenandrosta-1,4-dien-17β-ol-3-one, and
7-methyl-6-methylenandrost-1,4-dien-17β-ol-3-one.

EXAMPLE 2

6-methylenandrosta-1,4-diene-3,17-dione

[Compound (I): $R_1=R_2=R_3=R_4=H$]

To a stirred solution of 28.7 g (0.963 mol) of 6-methylenandrosta-1,4-dien-17β-ol-3-one in 700 ml of acetone, at −10° C., are added 35 ml of Jones reagent dropwise. When the addition is over, the reaction mixture is stirred for further 10 min and then carefully treated with 50 ml of isopropanol. After one hour of additional stirring, the resulting inorganic precipitate is filtered off and thoroughly washed with acetone. The combined filtrate and washings are stirred with 100 g of sodium bicarbonate for 1 hour, filtered and evaporated under vacuum. The resulting solid is taken up with 500 ml of water, filtered off, washed with water and then dried under vacuum at about 40° C., thus obtaining 25 g of a solid. Further purification by crystallization from 300 ml of a 65:35 mixture of ethanol and water gives 22.4 g (0.76 mol; yield 79%) of the title compound, m.p. 192°–195° C. Found C 81.01; H 8.16. $C_{20}H_{24}O_2$ requires: C 81.04; H 8.05; U.V. (EtOH, mμ): 247 (ε=13750).

NMR (CDCl$_3$, δ): 0.94 (3H, s), 1.17 (3H, s), 5.04 (2H, m), 6.18 (1H, br s), 6.25 (1H, dd), 7.09 (1H, d).

Using the same procedure and starting from the appropriate compound of formula (IV) one can prepare the following end-products:
1-methyl-6-methylenandrosta-1,4-diene-3,17-dione,
  m.p.: 178°–180° C.; Found: C 82.18; H 8.37. $C_{21}H_{26}O_2$ requires: C 81.25; H 8.44;
1-ethyl-6-methylenandrosta-1,4-diene-3,17-dione,
  Found: C 81.32; H 8.62. $C_{22}H_{28}O_2$ requires: C 81.44; H 8.70;
4-methyl-6-methylenandrosta-1,4-diene-3,17-dione;
  Found: C 81.15; H 8.32. $C_{21}H_{26}O_2$ requires: C 81.25; H 8.44;
4-chloro-6-methylenandrosta-1,4-diene-3,17-dione,
  m.p.: 148°–150° C.; Found: C 72.40, H 6.91, Cl 10.53; $C_{20}H_{23}ClO_2$ requires: C 72.61, H 7.01, Cl 10.72.
  N.M.R. (CDCl$_3$, δ): 0.84 (3H, s); 1.24 (3H, s); 5.13 (1H, s); 6.37 (1H, d); 7.08 (1H, d).
MS (m/z): 330.
4-bromo-6-methylenandrosta-1,4-diene-3,17-dione,
  Found: C 63.90; H 6.03; Br 21.15. $C_{20}H_{23}BrO_2$ requires: C 64.00; H 6.18; Br 21.29;
4-fluoro-6-methylenandrosta-1,4-diene-3,17-dione,
  Found: C 76.35; H 7.34; F 6.01. $C_{20}H_{23}FO_2$ requires: C 76.41; H 7.37; F 6.04.
4-chloro-1-methyl-6-methylenandrosta-1,4-diene-3,17-dione;
4-bromo-1-methyl-6-methylenandrosta-1,4-diene-3,17-dione;
4-fluoro-1-methyl-6-methylenandrosta-1,4-diene-3,17-dione, Found: C 76.75; H 7.62; F 5.71. $C_{21}H_{25}FO_2$ requires: C 76.80; H 7.67; F 5.97;

Analogously one can obtain the following 7- and/or 16-substituted derivatives as single epimers or as a mixture thereof
1,7-dimethyl-16-fluoro-6-methylenandrosta-1,4-diene-3,17-dione; Found: C 77.05, H 7.80, F 5.45. $C_{22}H_{27}FO_2$ requires: C 77.16, H 7.95, F 5.55.
16-fluoro-6-methylenandrosta-1,4-diene-3,17-dione;
16-fluoro-1-methyl-6-methylenandrosta-1,4-diene-3,17-dione;
1,7 dimethyl-6-methylenandrosta-1,4-diene-3,17-dione;
7 methyl-6-methylenandrosta-1,4-diene-3,17-dione;
16-fluoro-7-methyl-6-methylenandrosta-1,4-diene-3,17-dione;
16-fluoro-4-chloro-1,7-dimethyl-6-methylenandrosta-1,4-diene-3,17-dione, Found: C 70.05, H 6.89, Cl 9.32, F 4.99. $C_{22}H_{26}ClFO_2$ requires: C 70.11, H 6.95, Cl 9.41, F 5.04.
16-fluoro-4-chloro-6-methylenandrosta-1,4-diene-3,17-dione;
4,16-difluoro-6-methylenandrosta-1,4-diene-3,17-dione;
4-chloro-7-methyl-6-methylenandrosta-1,4-diene-3,17-dione;
4-fluoro-7-methyl-6-methylenandrosta-1,4-diene-3,17-dione;
16-fluoro-4-chloro-1-methyl-6-methylenandrosta-1,4-diene-3,17-dione;
4,16-difluoro-1-methyl-6-methylenandrosta-1,4-diene-3,17-dione;
4-chloro-1,7-dimethyl-6-methylenandrosta-1,4-diene-3,17-dione;
4-fluoro-1,7-dimethyl-6-methylenandrosta-1,4-diene-3,17-dione;

16-fluoro-4-chloro-7-methyl-6-methylenandrosta-1,4-diene-3,17-dione;

4,16-difluoro-7-methyl-6-methylenandrosta-1,4-diene-3,17-dione; and 4,16-difluoro-1,7-dimethyl-6-methylenandrosta-1,4-diene-3,17-dione.

We claim:

1. A process for the preparation of a compound of formula (I)

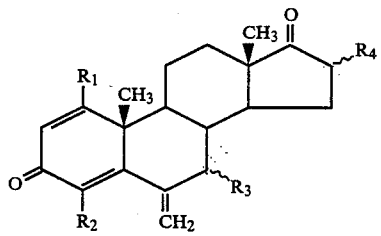

(I)

wherein
each of $R_1$ and $R_3$, independently, is hydrogen or $C_1$–$C_6$ alkyl;
$R_2$ is hydrogen, halogen or $C_1$–$C_6$ alkyl; and
$R_4$ is hydrogen or fluorine;
the process comprising reacting a compound of formula (II)

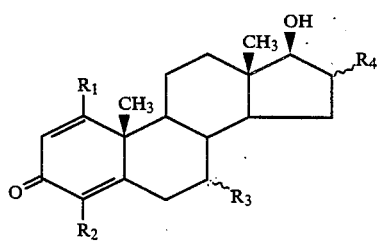

(II)

wherein $R_1$, $R_2$, $R_3$ and $R_4$ are as defined above, with a formaldehyde source and an amine of formula (III), or a salt thereof,

(III)

wherein
each R group, which may be the same or different, is lower alkyl, so as to obtain a compound of formula (IV)

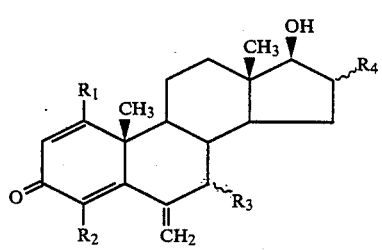

(IV)

wherein
$R_1$, $R_2$, $R_3$ and $R_4$ are as defined above, and oxidizing a compound of formula (IV) thus obtained, by methods known per se.

2. A process according to claim 1, wherein the compound of formula (II) is reacted in isopentanol at a temperature of at least 130° C. with the formaldehyde source and a salt formed between a hydrohalic acid and the amine of formula (III).

3. A process according to claim 1, wherein the compound of formula (II) is reacted with a Mannich salt obtained by reacting the formaldehyde source with a salt formed between a hydrohalic acid and the amine of formula (III).

4. A process according to any one of the preceding claims wherein the formaldehyde source is paraformaldehyde.

* * * * *